US012758326B2

(12) United States Patent
Schneider

(10) Patent No.: US 12,758,326 B2
(45) **Date of Patent: *Oct. 13, 2026**

(54) ELECTROMAGNETIC SENSOR

(71) Applicant: Northern Digital Inc., Waterloo (CA)

(72) Inventor: Mark Robert Schneider, Williston, VT (US)

(73) Assignee: Northern Digital Inc., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/209,097

(22) Filed: May 15, 2025

(65) Prior Publication Data

US 2025/0275811 A1 Sep. 4, 2025

Related U.S. Application Data

(63) Continuation of application No. 18/151,342, filed on Jan. 6, 2023, now Pat. No. 12,324,633.

(60) Provisional application No. 63/297,521, filed on Jan. 7, 2022.

(51) Int. Cl.

| | |
|---|---|
| ***A61B 34/20*** | (2016.01) |
| ***A61B 1/00*** | (2006.01) |
| ***A61B 5/00*** | (2006.01) |
| ***A61B 5/06*** | (2006.01) |

(52) U.S. Cl.

CPC .......... *A61B 34/20* (2016.02); *A61B 1/00167* (2013.01); *A61B 5/0084* (2013.01); *A61B 5/065* (2013.01); *A61B 2034/2051* (2016.02); *A61B 2034/2061* (2016.02)

(58) Field of Classification Search

CPC ............ A61B 34/20; A61B 2034/2055; A61B 2034/2061; A61B 2034/2051; A61B 5/0084; A61B 5/065; A61B 5/6852; A61B 5/062; A61B 1/009; A61B 1/00167

See application file for complete search history.

(56) References Cited

U.S. PATENT DOCUMENTS

| | | | |
|---|---|---|---|
| 6,380,732 | B1 | 4/2002 | Gilboa |
| 8,050,523 | B2 | 11/2011 | Younge et al. |
| 8,622,935 | B1 | 1/2014 | Leo |
| 9,366,536 | B2 | 6/2016 | Gray et al. |
| 9,618,741 | B2 | 4/2017 | Shimamoto et al. |
| 9,693,707 | B2 | 7/2017 | Chan et al. |

(Continued)

OTHER PUBLICATIONS

U.S. Appl. No. 63/227,799, Wiles et al., filed Jul. 30, 2021.

(Continued)

*Primary Examiner* — Boniface N Nganga
(74) *Attorney, Agent, or Firm* — Fish & Richardson P.C.

(57) ABSTRACT

A device comprising includes an insertable structure usable in a surgical theater, a fiber optic line extending through the structure, wherein a computer system is configured to determine a shape of the fiber optic line extending through the structure, and one or more electromagnetic sensors wrapped at least in part around one or more portions of the fiber optic line, wherein the computer system is configured to determine a position and orientation of the one or more electromagnetic sensors, wherein the computer system is configured to determine a shape and a position of the structure (Continued)

based on the determined shape of the fiber optic line extending through the structure and the determined position and orientation of the one or more electromagnetic sensors.

25 Claims, 5 Drawing Sheets

(56) References Cited

U.S. PATENT DOCUMENTS

| | | | | |
|---|---|---|---|---|
| 9,823,277 | B1 | 11/2017 | Lagakos et al. | |
| 9,926,780 | B2 | 3/2018 | Zeng et al. | |
| 10,194,831 | B2 | 2/2019 | Chan et al. | |
| 10,391,277 | B2 | 8/2019 | Rahimian et al. | |
| 10,603,472 | B2 | 3/2020 | Gliner et al. | |
| 10,905,855 | B2 | 2/2021 | Leo | |
| 11,109,776 | B2 | 9/2021 | Bharat et al. | |
| 12,324,633 | B2 * | 6/2025 | Schneider | A61B 1/009 |
| 2013/0131503 | A1 | 5/2013 | Schneider et al. | |
| 2016/0007842 | A1 | 1/2016 | Govari et al. | |
| 2016/0245670 | A1 | 8/2016 | Nelson et al. | |
| 2017/0123096 | A1 | 5/2017 | Wilson et al. | |
| 2017/0151027 | A1 | 6/2017 | Walker et al. | |
| 2017/0367776 | A1 | 12/2017 | Kwok et al. | |
| 2019/0094459 | A1 | 3/2019 | Froggatt et al. | |
| 2019/0320878 | A1 | 10/2019 | Duindam et al. | |
| 2020/0085514 | A1 | 3/2020 | Blumenkranz | |
| 2021/0138198 | A1 | 5/2021 | Leo | |
| 2021/0186648 | A1 | 6/2021 | Xia et al. | |
| 2021/0267696 | A1 | 9/2021 | Degertekin et al. | |

OTHER PUBLICATIONS

Chaudhary et al., “Magnetocuring of temperature failsafe epoxy adhesives,” Applied Materials Today, Dec. 2020, 21:100824, 13 pages.

Darwish et al., “Preparation and investigation of dc conductivity and relative permeability of epoxy/Li—Ni—Zn ferrite composites,” Journal of Magnetism and Magnetic Materials, Jul. 2015, 385:99-106.

Ha et al., “Robust Catheter Tracking by Fusing Electromagnetic Tracking, Fiber Bragg Grating and Sparse Fluoroscopic Images,” TechRxiv Preprint, May 2021, 12 pages.

Lu et al., “On-Chip Bondwire Magnetics with Ferrite-Epoxy Glob Coating for Power Systems on Chip,” Advances in Power Electronics, Jul. 16, 2008, 2008:678415, 9 pages.

Nourmohammadi et al., “Investigation of Noise Reduction and SNR Enhancement in Search Coil Magnetometers at Low Frequencies,” CoRR, Submitted on Sep. 24, 2014, arXiv:1409.7267v1, 6 pages.

Soft Ferrites: Properties and Applications, 1st ed., Snelling, 1969, 411 pages.

Song et al., “Electromagnetic Positioning for Tip Tracking and Shape Sensing of Flexible Robots,” IEEE Sensors Journal, Aug. 2015, 15(8):4565-4575.

Tran et al., “3D Catheter Shape Reconstruction Using Electromagnetic and Image Sensors,” Journal of Medical Robotics Research, Mar. 2017, 2(3):1740009, 13 pages.

* cited by examiner

ELECTROMAGNETIC SENSOR

CROSS-REFERENCE TO RELATED APPLICATIONS

This application is a continuation application of and claims the benefit of priority under 35 U.S.C. § 120 to U.S. application Ser. No. 18/151,342, filed on Jan. 6, 2023, which claims priority under 35 USC § 119(e) to U.S. Patent Application Ser. No. 63/297,521, filed on Jan. 7, 2022, the entire contents of each application is hereby incorporated by reference.

TECHNICAL FIELD

This disclosure relates to an electromagnetic (EM) sensor, and more particularly, to a hybrid EM-optical sensor.

BACKGROUND

Electromagnetic Tracking (EMT) systems are used to aid in locating instruments and anatomy in medical procedures. These systems utilize a magnetic transmitter in proximity to one or more magnetic sensors. The one or more sensors can be spatially located relative to the transmitter. The one or more sensors may be equipped for EM and/or optical tracking using, for example, fiber optic shape sensing (FOSS).

SUMMARY

Tracking systems that provide pose (i.e., position and orientation) information in medical procedures are used to locate instruments and make measurements with respect to patient anatomy. These medical procedures span many domains and can include surgical interventions, diagnostic procedures, imaging procedures, and radiation treatment. Some common offerings are either a) based on tools that are uniquely identifiable and tracked by optical cameras, and/or b) electromagnetic sensors that measure a field from a magnetic field generator.

In some implementations, a catheter or a guidewire may be equipped for shape sensing, including fiber optic shape sensing (FOSS) and pose measurements by one or more electromagnetic (EM) sensors. Using such a combination of sensors, an absolute measure of pose of the catheter can be determined. Such shape sensing can be used for procedures such as endoscopy, vascular catheterization, GI and pulmonary studies, etc.

In an aspect, a system includes a computer system comprising a processor to execute instructions, an insertable structure usable in a surgical theater, a fiber optic line extending through the structure, wherein the computer system is configured to determine a shape of the fiber optic line extending through the structure, and one or more electromagnetic sensors wrapped at least in part around one or more portions of the fiber optic line, wherein the computer system is configured to determine a position and orientation of the one or more electromagnetic sensors, and wherein the computer system is configured to determine a shape and a position of the structure based on the determined shape of the fiber optic line extending through the structure and the determined position and orientation of the one or more electromagnetic sensors.

Implementations can include one or more of the following features.

In some implementations, the system includes a field generator in communication with the one or more electromagnetic sensors.

In some implementations, the field generator resides beneath a patient.

In some implementations, the one or more electromagnetic sensors provide a reference coordinate system for the fiber optic line.

In some implementations, one or more segments of the fiber optic line comprise one or more Fiber Bragg Gratings to produce strain measurements.

In some implementations, a strain experienced by one or more segments of the fiber optic line is determined from Rayleigh scattering.

In some implementations, the determined shape of the fiber optic line is compensated for temperature.

In some implementations, one of the one or more electromagnetic sensors has a solenoidal geometry that includes a plurality of substantially orbital turns.

In some implementations, one of the one or more electromagnetic sensors has a saddle geometry that includes a plurality of substantially 90 degree turns.

In some implementations, a central axis of the one or more electromagnetic sensors is aligned with a central axis of the fiber optic line.

In some implementations, the one or more electromagnetic sensors are wrapped directly around the fiber optic line.

In some implementations, the one or more electromagnetic sensors are wrapped around a core that surrounds the fiber optic line.

In some implementations, the core includes at least one of a ferrite material, a mu-metal material, or a permalloy material.

In some implementations, one of the one or more electromagnetic sensors is adhered to the fiber optic by a ferrite epoxy.

In another aspect, a device includes an insertable structure usable in a surgical theater, a fiber optic line extending through the structure, wherein a computer system is configured to determine a shape of the fiber optic line extending through the structure, and one or more electromagnetic sensors wrapped at least in part around one or more portions of the fiber optic line, wherein the computer system is configured to determine a position and orientation of the one or more electromagnetic sensors, wherein the computer system is configured to determine a shape and a position of the structure based on the determined shape of the fiber optic line extending through the structure and the determined position and orientation of the one or more electromagnetic sensors.

Implementations can include one or more of the following features.

In some implementations, the one or more electromagnetic sensors provide a reference coordinate system for the fiber optic line.

In some implementations, one or more segments of the fiber optic line comprise one or more Fiber Bragg Gratings to produce strain measurements.

In some implementations, a strain experienced by one or more segments of the fiber optic line is determined from Rayleigh scattering.

In some implementations, the determined shape of the fiber optic line is compensated for temperature.

In some implementations, one of the one or more electromagnetic sensors has a solenoidal geometry that includes a plurality of substantially orbital turns.

In some implementations, one of the one or more electromagnetic sensors has a saddle geometry that includes a plurality of substantially 90-degree turns.

In some implementations, a central axis of each of the one or more electromagnetic sensors aligns with a central axis of the fiber optic line.

In some implementations, the one or more electromagnetic sensors are wrapped directly around the fiber optic line.

In some implementations, the one or more electromagnetic sensors are wrapped around a core that surrounds the fiber optic line.

In some implementations, the core comprises at least one of a ferrite material, a mu-metal material, or a permalloy material.

In some implementations, one of the one or more electromagnetic sensors is adhered to the fiber optic line by a ferrite epoxy.

In some implementations, the structure comprises a catheter and/or guidewire Implementations may provide one or more of the following advantages.

In some implementations, the shape of the fiber optic line can be determined with improved accuracy by having the EM sensors not offset from an axis of the fiber optic line. In other words, the EM sensors and the fiber optic line may share a common axis.

In some implementations, by including EM sensors in the device, an absolute measure of the pose of the fiber optic line (e.g., rather than a relative measure of the pose) can be determined. In turn, the shape of the fiber optic line relative to a patient can be determined.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference numbers and designations in the various drawings indicate like elements.

DETAILED DESCRIPTION

Figure 1:
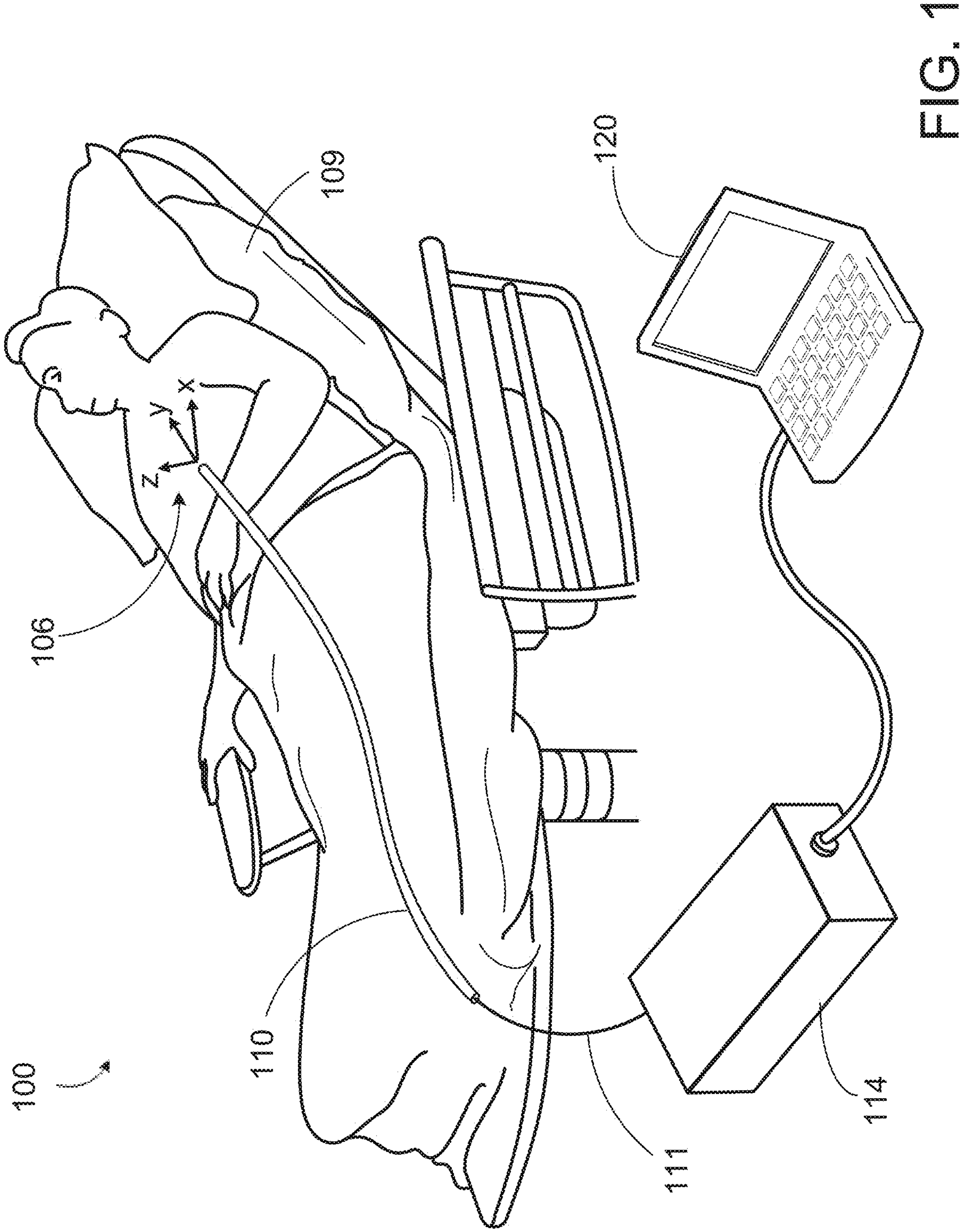
FIG. 1 is a schematic diagram of an example Electromagnetic Tracking (EMT) system that includes a fiber optic line for fiber optic shape sensing.

Five or Six Degree of Freedom (5 or 6DOF) Tracking Systems (e.g., tracking systems that employ 5DOF or 6DOF sensors) can be used in medical contexts to track one or more objects (e.g., a piece of medical equipment, a robotic arm, etc.), thereby allowing the respective three-dimensional location, orientation, etc. of the object or objects to be known to a medical professional (e.g., a surgeon). Such tracking can be used for guidance purposes in image-guided procedures and in some cases may allow for reduced reliance on other imaging modalities, such as fluoroscopy, which can expose the patient to health risk of ionizing radiation. Such systems are described in U.S. Application Ser. No. 63/227,799, entitled "TRACKING SYSTEM", filed on Jul. 30, 2021, which is hereby incorporated by reference in its entirety.

In some implementations, the 5DOF or 6DOF Tracking System is an electromagnetic tracking system or an optical tracking system. In some implementations, the 5DOF or 6DOF Tracking System employs both electromagnetic and optical components.

In general, in 5DOF or 6DOF tracking systems that include electromagnetic tracking functionality (e.g., 5DOF or 6DOF tracking systems), a transmitter having one or more coils is configured to generate an EM field (e.g., an alternating current (AC) EM field, a direct current (DC) EM field, AC and DC EM fields in combination, etc.). One or more multiplexing schemes may be implemented by the tracking system. One multiplexing scheme is time division multiplexing (TDM), e.g., transmitting and receiving signals such that each signal appears for a fraction of time in an alternating pattern. For the tracking system, TDM can be used for AC EM fields, DC EM fields, AC and DC EM fields in combination, etc. Another type of multiplexing scheme that can be employed is frequency division multiplexing (FDM), e.g., transmitting and receiving signals divided into a series of non-overlapping frequency bands. Typically, FDM is used with AC EM fields. Other transmitter technologies that generate varying fields, such as spinning magnets, can also be used, as is known in the art. One or more sensors having one or more coils that are in proximity to the generated EM field is configured to measure characteristics of the generated EM field. The measured characteristics of the EM field depend upon the position and orientation of the sensors relative to the transmitter. For example, when the sensors are located at a particular position and orientation, the EM field at that particular location may have particular characteristics. The sensors can measure the characteristics of the EM field and provide such measurements (e.g., via sensor signals) to a computing device (e.g., a computer system). Using information related to the generated EM field and the sensor signals received from the sensors, the computing device can determine the position and/or orientation of the sensors. By employing this technique, the position, orientation, etc. of a medical device that contains the sensor can be determined and used by the computing device (e.g., the computing device can graphically represent the medical device, the sensor, registered medical images, etc.).

In general, such 5DOF or 6DOF tracking systems can also be equipped with fiber optic shape sensing (FOSS) capabilities. For example, while one or more EM sensors may be able to provide pose information for two discrete points, FOSS can be used to ascertain shape information for a continuous segment (e.g., a segment of a catheter), as described in more detail below.

FIG. 1 shows an example of a system, for example, an electromagnetic tracking (EMT) system 100 that is implemented in the surgical environment (e.g., a surgical theater). The system 100 is configured to determine the location of one or more electromagnetic sensors, such as one or more sensors embedded in a catheter or another structure (e.g., surgical equipment such as a scalpel, probe, guidewire, etc.) located within a patient. The electromagnetic tracking techniques employed for tracking medical devices, for example, may be similar to those described in U.S. patent application Ser. No. 13/683,703, entitled "Tracking a Guidewire", filed on Nov. 21, 2012, which is hereby incorporated by reference in its entirety. The electromagnetic tracking techniques can employ a computer component, a transmitter excitation component and a receiving component. Under computer command and control, a multi axis transmitter assembly can have each of its axes energized by drive electronics (e.g., DC drive electronics, AC drive electronics, etc.) to transmit waveforms (e.g., symmetrical, sequentially excited, non-overlapping square DC-based waveforms). These are received through the air or tissue by one or more sensors that conveys these signals to signal processing electronics within the electromagnetic tracking system electronics. The computer in the electromagnetic tracking system electronics can execute various processing operations; for example measure the rising edge and steady state of each axes' sequential waveform (e.g., using an integrator) so that a result (e.g., an integrated result) may be measured at the end of the steady state period. The computer can further control the transmitter drive electronics to operate the transmitter and receives signals from the signal processing electronics for one or more processes (e.g., the signal integration process), the end result being calculation of the sensor's position and orientation in three-dimensional space with significantly reduced eddy current distortion while providing improved compensation for sensor drift with respect to the Earth's stationary magnetic field and power-line induced noise.

Figure 2:
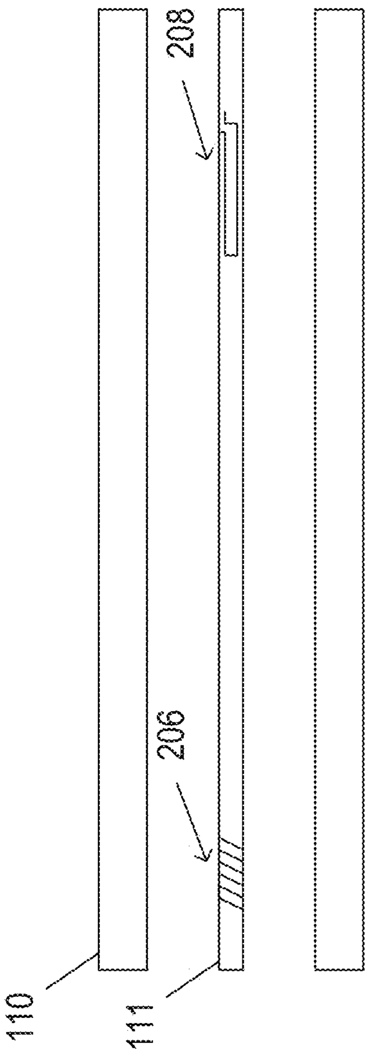
FIG. 2 shows a cross-sectional view of a catheter that includes the fiber optic line of FIG. 1 and electromagnetic sensors.

In this example, a catheter 110 is inserted in a patient. The catheter 110 includes two EM sensors (206, 208 of FIG. 2) for allowing the catheter to be tracked by the system 100 such that the pose of the EM sensors 206, 208 can be used to define a reference coordinate system 106. In this way, the location of the EM sensors relative to a patient is known. A relevant portion of the end of the catheter showing the two EM sensors 206, 208 is shown in FIG. 2, described in more detail below.

A field generator 109 is positioned in the tracking environment. In the illustrated example, the field generator 109 resides beneath the patient. The field generator may be located under a surface that the patient is positioned on, embedded in a table that the patient lays upon, etc., or the field generator 109 may be positioned partially or completely elsewhere in the environment. The field generator 109 is configured to emit electromagnetic fields that are sensed by the accompanying electromagnetic sensors (e.g., EM sensors 206, 208). In some implementations, the field generator 109 is an NDI Aurora Tabletop Field Generator (TTFG), although other field generator techniques and/or designs can be employed, as known to those skilled in the art.

A fiber optic line 111 is extended within the catheter 110. The shape of the fiber optic line 111 can be tracked. As described above, the EM sensors 206, 208 provide an absolute measure of pose (e.g., rather than a relative one), so a reference point is provided for the fiber optic line 111. That is, the fiber optic line 111 can be tracked relative to one or both of the EM sensors 206, 208. The fiber optic line 111 is tracked based on a fiber optic signal. In particular, an interrogator 114 can send and receive fiber optic signals to the tip of the fiber optic line 111 that are indicative of a relative pose (e.g., location and orientation) or a shape of the fiber optic line 111. For example, the exact shape of the fiber optic line 111 may be determined based on the fiber optic signals transmitted to and from the interrogator 114.

In some implementations, the interrogator 114 is an optoelectronic data acquisition system that provides measurements of the light reflected through the optical fiber. The interrogator 114 provides these measurements to the computing device (e.g., the computing device 120), as described in more detail below.

There are means by which optical transducers built into an optical fiber can produce measurements (for example wavelength measurements) that can be used to estimate pose information along the length of the fiber. In some implementations, the fiber optic line 111 may be equipped with a series of Fiber Bragg Gratings (FBG), which amount to a periodic change in the refractive index manufactured into the optical fiber. In some implementations, the fiber optic line 111 may rely on Rayleigh scattering, which is a natural process arising from microscopic imperfections in the fiber. Techniques using FBG, Rayleigh scattering, or both have the capacity to reflect specific wavelengths of light that may correspond to strain or changes in temperature within the fiber. Deformations in the fiber optic line 111 cause these wavelengths to shift, and the wavelength shift can be measured by the interrogator 114. The technology used by the interrogator 114 to measure wavelength shift can be Wavelength-Division Multiplexing (WDM) or Optical Frequency-Domain Reflectometry (OFDR). In doing so, the shape of the fiber optic line 111 can be estimated by an algorithm being executed on the computing device 120.

At each periodic refraction change, a small amount of light is reflected. All the reflected light signals combine coherently to one large reflection at a particular wavelength when the grating period is approximately half the input light's wavelength. This is referred to as the Bragg condition, and the wavelength at which this reflection occurs is called the Bragg wavelength. Light signals at wavelengths other than the Bragg wavelength, which are not phase matched, are essentially transparent.

Therefore, light propagates through the grating with negligible attenuation or signal variation. Only those wavelengths that satisfy the Bragg condition are affected and strongly back-reflected. The ability to accurately preset and maintain the grating wavelength is a fundamental feature and advantage of Fiber Bragg gratings.

The central wavelength of the reflected component satisfies the Bragg relation: $\lambda_{Bragg}=2\ n\Lambda$, with n the index of refraction and $\Lambda$ the period of the index of refraction variation of the FBG. Due to the temperature and strain dependence of the parameters n and $\Lambda$, the wavelength of the reflected component will also change as function of temperature and/or strain. This dependency can be utilized for determining the temperature or strain from the reflected FBG wavelength.

Tracking systems are frequently accompanied by computing equipment and displays to process and visualize the measurement data. For example, in a surgical intervention, a surgical tool measured by the tracking system can be visualized with respect to the anatomy marked up with annotations from the pre-operative plan. Another such example may include an X-ray image annotated with live updates from a tracked catheter.

By affixing a fiber instrumented as such, a new sensing/measurement paradigm is possible for 5DOF or 6DOF tracking systems, enabling the pose and shape measurements along the fiber in the co-ordinate space of the 5DOF or 6DOF tracking system. Additionally, in an optical tracking supported procedure, this can allow one to take pose measurements outside of the measurement volume or line-of-sight of the optical tracking system. In the context of an EMT supported procedure, this can allow one to take pose measurements in a region with high metal distortion where EMT sensors would normally perform poorly, or one can use the fiber measurements to correct for electromagnetic/metal distortion.

FIG. 2 shows a cross-sectional view of the catheter 110 of FIG. 1. The fiber optic line 111 runs through the catheter 110. The fiber optic line 111 includes two EM sensors, a first, solenoidal EM sensor 206 and a second, saddle-shaped EM sensor 208. By providing two EM sensors 206, 208 of the defined shapes, 6DOF tracking can be provided by the system 100. The components of the catheter 110 and the components internal to the catheter (e.g., the fiber optic line 111 and the EM sensors 206, 208) can be generally referred to as a device, or more specifically, as a medical device.

While the EM sensors 206, 208 as shown in FIG. 2 can provide 6DOF, a 5DOF tracking system may instead be provided with a different configuration of EM sensors. For example, 5DOF tracking may be enabled if only one EM sensor is provided, and/or if multiple EM sensors of the same type are provided (e.g., two solenoidal sensors or two saddle-shaped sensors). In some implementations, 6DOF tracking can be enabled if multiple EM sensors of the same type are provided (e.g., two saddle-shaped sensors that are 90 degrees apart, perpendicular). Further, the distance between the EM sensors may be determinative of whether 5DOF or 6DOF tracking is possible. For example, if the sensors are separated by more than a threshold distance, then 5DOF tracking may be employed by the system. Thus, to ensure 6DOF tracking, the two EM sensors should be within a threshold distance of one another (e.g., in the order of millimeters). In some implementations, the two EM sensors 206, 208 may be located around one another (e.g., one wrapped on top of the other), being insulated from one another. In some implementations, the EM sensors 206, 208 magnetically point along different axes when they are wrapped around one another. In some implementations, the EM sensors 206, 208 may be displaced by a very small distance. In some implementations, when the EM sensors 206, 208 are relatively close to one another, the resultant pose determination may be relatively more accurate.

In some implementations, the sensors 206, 208 can be used to provide 5DOF or 6DOF tracking of structures other than catheters. For example, the sensors 206, 208 can be incorporated into a guidewire. The sensors 206, 208 can be incorporated in a variety of positions in the structures. In some implementations, the sensors can be incorporated into a robotic arm (e.g., a robotic arm used for robotic surgeries). A robotic arm measured by the tracking system can be visualized with respect to the anatomy marked up with annotations from the pre-operative plan.

Figure 3C:
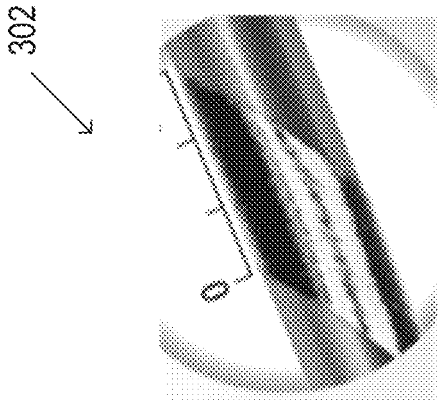
FIG. 3C shows another example of an electromagnetic sensor.
Figure 3B:
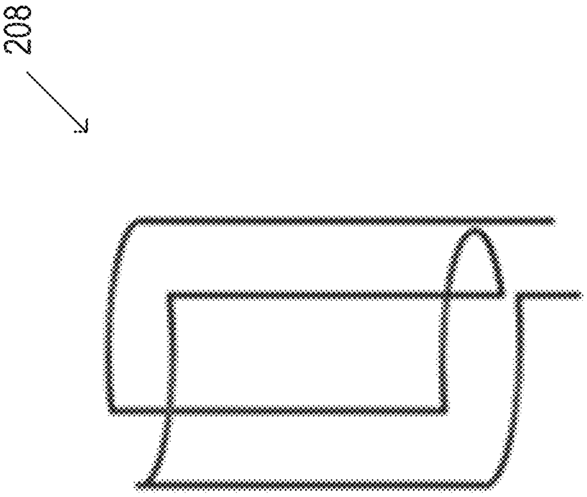
FIGS. 3A-B show the electromagnetic sensors of FIG. 2.
Figure 3A:
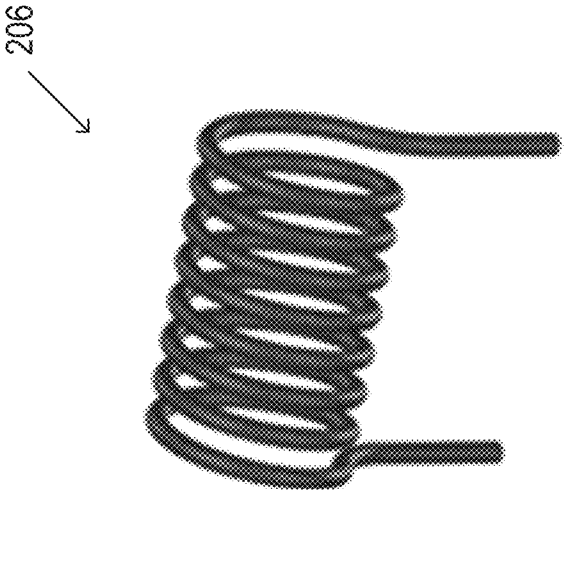

FIG. 3A shows a perspective view of the solenoidal EM sensor 206 of FIG. 2, and FIG. 3B shows a perspective view of the saddle-shaped EM sensor 208 of FIG. 2.

The solenoidal EM sensor 206 of FIG. 3A includes a plurality of substantially orbital turns, and the saddle-shaped EM sensor 208 of FIG. 3B includes a plurality of substantially 90-degree turns. In some implementations, as shown, the EM sensors 206, 208 are wrapped directly on/around the fiber optic line 111, without any attachment device and/or fixtures being required (e.g., excluding wires attached to the EM sensors 206, 208 and/or any potential adhesive, as described in more detail below). For example, no mechanical claptraps holding the EM sensors 206, 208 to the catheter 110 need be employed in the systems and devices described herein. As such, the EM sensors 206, 208 share a common axis with the fiber optic line 111 in such examples (e.g., the EM sensors 206, 208 are not offset from the fiber optic line 111). Eliminating such fixtures, which may otherwise offset and/or distort the position of the EM sensor, allows for more accurate shape sensing because the EM sensors 206, 208 are in line with the fiber optic line 111 (e.g., not alongside it). In some implementations, the EM sensors 206, 208 can be wrapped around a separate hollow core, which is then provided over the fiber optic line 111.

The coils of the EM sensors 206, 208 can be made from a material such as copper, and may be wound on polyimide tubing, which can then be glued on the fiber optic line 111.

In some implementations, the coils can be wound on a core of a material that increases sensor sensitivity, such as a ferrite, a mu-metal, or a permalloy or other amorphous metal with high permeability. On the other hand, when the coils are wound directly onto the fiber optic line 111, a smallest possible diameter can be provided. To avoid and/or minimize negative consequences to sensor sensitivity of wrapping the coils directly on the fiber optic line 111, a magnetic glue may be used to assist in affixing one or both of the EM sensors 206, 208 to the fiber optic line 111. Such a glue could be made from ferrite epoxy. In some implementations, the magnetic glue could be cured using a magnetic field (e.g., to speed up assembly time).

FIG. 3C shows another example of an EM sensor 302 that can be employed by the system 100. The EM sensor 302 may be similar to the solenoidal sensor 206 of FIG. 3A, except the turns of the sensor can be provided at an angle. Due to the particular sensor geometry, 6DOF tracking can be provided if two of the EM sensors 302 are provided on the fiber optic line 111. In implementations in which two EM sensors 302 are used (e.g., to achieve 6DOF tracking), the two sensors 302 may be rotationally offset from one another, e.g., by 90°.

While the systems and devices described herein related to tracking a catheter using a fiber optic line and two EM sensors, similar techniques may also be employed for tracking a guidewire. For example, the fiber optic line with the EM sensors wrapped around it can be affixed to a guidewire for tracking the pose and shape of the guidewire.

As described above, the operation of the system 100 can be controlled by a computing device 120 (e.g., a computer system). In particular, the computing device 120 can be used to interface with the system 100 and cause the locations/orientations of the EM sensors 206, 208 and the fiber optic line 111 to be determined. In this way, the computer system is configured to determine a shape of the fiber optic line extending through the catheter, a position and orientation of the solenoidal EM sensor, and the position and orientation of the saddle-shaped EM sensor. In particular, the computer system is configured to determine a shape, position, and orientation of the catheter based on the determined shape of the fiber optic line extending through the catheter and the determined positions and orientations of the EM sensors.

Figure 4:
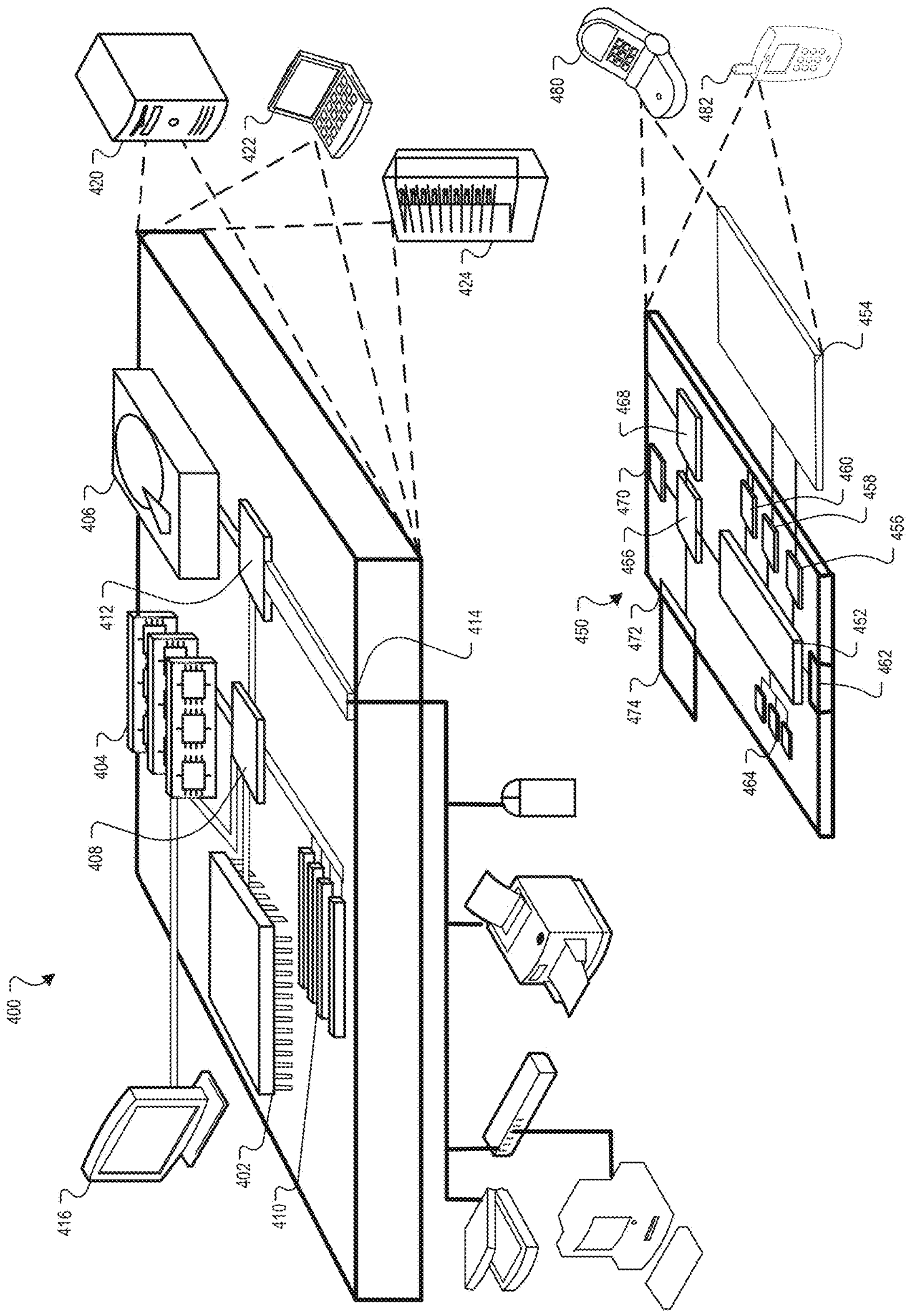
FIG. 4 shows a schematic diagram of an example computer system.

FIG. 4 shows an example computing device 400 and an example mobile computing device 450, which can be used to implement the techniques described herein. For example, the computing device 400 may be implemented as the computing device 120 of FIG. 1. Computing device 400 is intended to represent various forms of digital computers, including, e.g., laptops, desktops, workstations, personal digital assistants, servers, blade servers, mainframes, and other appropriate computers. Computing device 450 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 400 includes processor 402, memory 404, storage device 406, high-speed interface 408 connecting to memory 404 and high-speed expansion ports 410, and low speed interface 412 connecting to low speed bus 414 and storage device 406. Each of components 402, 404, 406, 408, 410, and 412, are interconnected using various busses, and can be mounted on a common motherboard or in other manners as appropriate. Processor 402 can process instructions for execution within computing device 400, including instructions stored in memory 404 or on storage device 406, to display graphical data for a GUI on an external input/output device, including, e.g., display 416 coupled to high-speed interface 408. In some implementations, multiple processors and/or multiple buses can be used, as appropriate, along with multiple memories and types of memory. In addition, multiple computing devices 400 can be connected, with each device providing portions of the necessary operations (e.g., as a server bank, a group of blade servers, a multi-processor system, etc.).

Memory 404 stores data within computing device 400. In some implementations, memory 404 is a volatile memory unit or units. In some implementation, memory 604 is a non-volatile memory unit or units. Memory 404 also can be another form of computer-readable medium, including, e.g., a magnetic or optical disk.

Storage device 406 is capable of providing mass storage for computing device 400. In some implementations, storage device 406 can be or contain a computer-readable medium, including, e.g., a floppy disk device, a hard disk device, an optical disk device, a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 404, storage device 406, memory on processor 402, and the like.

High-speed controller 408 manages bandwidth-intensive operations for computing device 400, while low speed controller 412 manages lower bandwidth-intensive operations. Such allocation of functions is an example only. In some implementations, high-speed controller 408 is coupled to memory 404, display 416 (e.g., through a graphics processor or accelerator), and to high-speed expansion ports 410, which can accept various expansion cards (not shown). In some implementations, the low-speed controller 412 is coupled to storage device 406 and low-speed expansion port 414. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router (e.g., through a network adapter).

Computing device 400 can be implemented in a number of different forms, as shown in FIG. 4. For example, the computing device 400 can be implemented as standard server 420, or multiple times in a group of such servers. The computing device 400 can also can be implemented as part of rack server system 424. In addition or as an alternative, the computing device 400 can be implemented in a personal computer (e.g., laptop computer 422). In some examples, components from computing device 400 can be combined with other components in a mobile device (e.g., the mobile computing device 450). Each of such devices can contain one or more of computing device 400, 450, and an entire system can be made up of multiple computing devices 400, 450 communicating with each other.

Computing device 450 includes processor 452, memory 464, and an input/output device including, e.g., display 454, communication interface 466, and transceiver 468, among other components. Device 450 also can be provided with a storage device, including, e.g., a microdrive or other device, to provide additional storage. Components 450, 452, 464, 454, 466, and 468, may each be interconnected using various buses, and several of the components can be mounted on a common motherboard or in other manners as appropriate.

Processor 452 can execute instructions within computing device 450, including instructions stored in memory 464. The processor 452 can be implemented as a chipset of chips that include separate and multiple analog and digital processors. The processor 452 can provide, for example, for the coordination of the other components of device 450, including, e.g., control of user interfaces, applications run by device 450, and wireless communication by device 450.

Processor 452 can communicate with a user through control interface 458 and display interface 456 coupled to display 454. Display 454 can be, for example, a TFT LCD (Thin-Film-Transistor Liquid Crystal Display) or an OLED (Organic Light Emitting Diode) display, or other appropriate display technology. Display interface 456 can comprise appropriate circuitry for driving display 454 to present graphical and other data to a user. Control interface 458 can receive commands from a user and convert them for submission to processor 452. In addition, external interface 462 can communicate with processor 442, so as to enable near area communication of device 450 with other devices. External interface 462 can provide, for example, for wired communication in some implementations, or for wireless communication in some implementations. Multiple interfaces also can be used.

Memory 464 stores data within computing device 450. Memory 464 can be implemented as one or more of a computer-readable medium or media, a volatile memory unit or units, or a non-volatile memory unit or units. Expansion memory 474 also can be provided and connected to device 450 through expansion interface 472, which can include, for example, a SIMM (Single In Line Memory Module) card interface. Such expansion memory 474 can provide extra storage space for device 450, and/or may store applications or other data for device 450. Specifically, expansion memory 474 can also include instructions to carry out or supplement the processes described above and can include secure data. Thus, for example, expansion memory 474 can be provided as a security module for device 450 and can be programmed with instructions that permit secure use of device 450. In addition, secure applications can be provided through the SIMM cards, along with additional data, including, e.g., placing identifying data on the SIMM card in a non-hackable manner.

The memory 464 can include, for example, flash memory and/or NVRAM memory, as discussed below. In some implementations, a computer program product is tangibly embodied in a data carrier. The computer program product contains instructions that, when executed, perform one or more methods. The data carrier is a computer- or machine-readable medium, including, e.g., memory 464, expansion memory 474, and/or memory on processor 452, which can be received, for example, over transceiver 468 or external interface 462.

Device 450 can communicate wirelessly through communication interface 466, which can include digital signal processing circuitry where necessary. Communication interface 466 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 468. In addition, short-range communication can occur, including, e.g., using a Bluetooth®, WiFi, or other such transceiver (not shown). In addition, GPS (Global Positioning System) receiver module 470 can provide additional navigation- and location-related wireless data to device 450, which can be used as appropriate by applications running on device 450.

Device 450 also can communicate audibly using audio codec 460, which can receive spoken data from a user and convert it to usable digital data. Audio codec 460 can likewise generate audible sound for a user, including, e.g., through a speaker, e.g., in a handset of device 450. Such sound can include sound from voice telephone calls, recorded sound (e.g., voice messages, music files, and the like) and also sound generated by applications operating on device 450.

Computing device 450 can be implemented in a number of different forms, as shown in FIG. 4. For example, the computing device 450 can be implemented as cellular telephone 480. The computing device 450 also can be implemented as part of smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system. This includes at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described herein can be implemented on a computer having a display device (e.g., a CRT (cathode ray tube) or LCD (liquid crystal display) monitor) for presenting data to the user, and a keyboard and a pointing device (e.g., a mouse or a trackball) by which the user can provide input to the computer. Other kinds of devices can be used to provide for interaction with a user as well. For example, feedback provided to the user can be a form of sensory feedback (e.g., visual feedback, auditory feedback, or tactile feedback). Input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such backend, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the components described herein can be separated, combined or incorporated into a single or combined component. The components depicted in the figures are not intended to limit the systems described herein to the software architectures shown in the figures.

Figure 5:
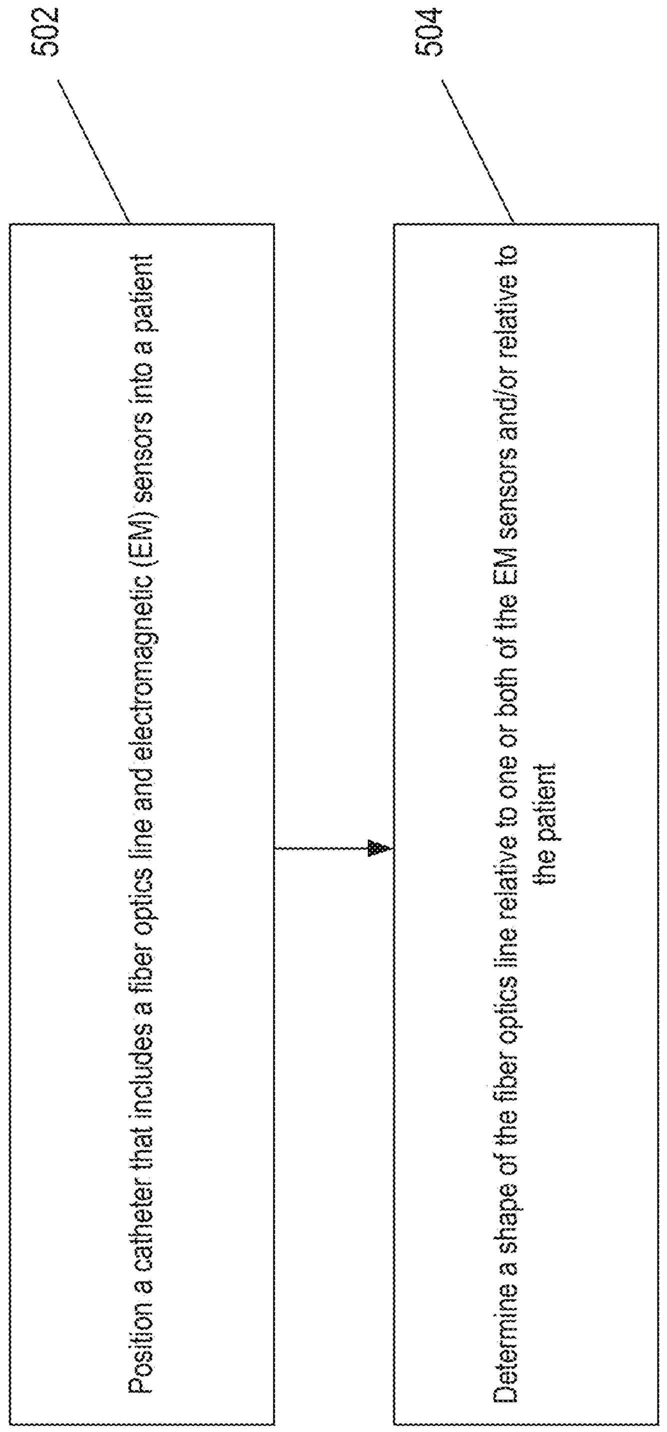
FIG. 5 is a flowchart showing an exemplary procedure that could be performed by the EMT system of FIG. 1.

FIG. 5 shows a flowchart of an exemplary procedure that could be performed by the system 100 of FIG. 1.

At 502, a structure (e.g., a catheter, a guidewire, etc.) is positioned (e.g., within a patient). For example, the structure can include a fiber optic line extending through the structure and electromagnetic (EM) sensors (e.g., two EM sensors). For example, the EM sensors can be located in an end of the structure. For example, the structure can be similar to the catheter 110 of FIG. 1.

At step 504, a shape of the fiber optic line relative to one or both of the EM sensors is determined. For example, the fiber optic line may be connected to a computing device and/or an interrogator that allow for positionally tracking the fiber optic line. In other words, the shape of the fiber optic line can be determined. For example, the fiber optic line can be similar to the fiber optic line 111 of FIG. 1, which transmits signals to and receives signals from the interrogator 114. In some implementations, the interrogator 114 provides these signals to a computing device (e.g., the computing device 120). As described above, deformations in the fiber optic line 111 cause wavelengths to shift, and the wavelength shift can be measured by the interrogator 114 to determine a shape of the fiber optic line. For example, the technology used by the interrogator 114 to measure wavelength shift can be Wavelength-Division Multiplexing (WDM) or Optical Frequency-Domain Reflectometry (OFDR).

The EM sensors may be wrapped around the fiber optic line and/or wrapped around a separate core that is then provided around the fiber optic line. For example the EM sensors can be similar to those illustrated in FIG. 2.

When the shape of the fiber optic line relative to one or both of the EM sensors is determined, an absolute measure of pose (e.g., as opposed to a relative measure of pose) of the fiber optic line is determined. Thus, the shape of the fiber optic line relative to the patient can in turn be determined. In some implementations, the reference coordinate system 106 can be used to represent an absolute coordinate system for a portion of the fiber optic line and/or one of the EM sensors.

A number of embodiments have been described. Nevertheless, it will be understood that various modifications may be made without departing from the spirit and scope of the disclosure. Accordingly, other embodiments are within the scope of the following claims.

What is claimed is:

1. A system comprising:

a computer system comprising a processor to execute instructions;

an insertable structure usable in a medical environment;

a fiber optic line extending through the structure; and two or more electromagnetic sensors wrapped at least in part around one or more portions of the fiber optic line, wherein the computer system is configured to determine a position and orientation of the two or more electromagnetic sensors, wherein the two or more electromagnetic sensors comprise:

a first electromagnetic sensor comprising a solenoidal geometry, the first electromagnetic sensor being wrapped at least in part around one of the one or more portions of the fiber optic line; and a second electromagnetic sensor comprising a saddle geometry, the second electromagnetic sensor being wrapped at least in part around the first electromagnetic sensor; and wherein the computer system is configured to determine a shape of the structure.

2. The system of claim 1, further comprising a field generator in communication with the two or more electromagnetic sensors.

3. The system of claim 2, wherein the field generator is configured to reside beneath a patient.

4. The system of claim 1, wherein the two or more electromagnetic sensors provide a reference coordinate system for the fiber optic line.

5. The system of claim 1, wherein one or more segments of the fiber optic line comprise one or more Fiber Bragg Gratings to produce strain measurements.

6. The system of claim 1, wherein a strain experienced by one or more segments of the fiber optic line is determined from Rayleigh scattering.

7. The system of claim 1, wherein the determined shape of the fiber optic line is compensated for temperature.

8. The system of claim 1, wherein a central axis of one of the two or more electromagnetic sensors is aligned with a central axis of the fiber optic line.

9. The system of claim 1, wherein the first electromagnetic sensor is wrapped directly around the fiber optic line.

10. The system of claim 1, wherein the two or more electromagnetic sensors are wrapped around a core that surrounds the fiber optic line.

11. The system of claim 10, wherein the core includes at least one of a ferrite material, a mu-metal material, or a permalloy material.

12. The system of claim 1, wherein one of the two or more electromagnetic sensors is adhered to the fiber optic by a ferrite epoxy.

13. A device comprising:

an insertable structure usable in a medical environment;

a fiber optic line extending through the structure; and two or more electromagnetic sensors wrapped at least in part around one or more portions of the fiber optic line, wherein the two or more electromagnetic sensors comprise:

a first electromagnetic sensor comprising a solenoidal geometry and wrapped at least in part around one of the one or more portions of the fiber optic line; and a second electromagnetic sensor comprising a saddle geometry, the second electromagnetic sensor being wrapped at least in part around the first electromagnetic sensor.

14. The device of claim 13, wherein the one of the two or more electromagnetic sensors provide a reference coordinate system for the fiber optic line.

15. The device of claim 13, wherein one or more segments of the fiber optic line comprise one or more Fiber Bragg Gratings to produce strain measurements.

16. The device of claim 13, wherein a strain experienced by one or more segments of the fiber optic line is determined from Rayleigh scattering.

17. The device of claim 13, wherein the saddle geometry comprises a plurality of 90 degree turns.

18. The device of claim 13, wherein a central axis of each of the two or more electromagnetic sensors aligns with a central axis of the fiber optic line.

19. The device of claim 13, wherein the first electromagnetic sensor is wrapped directly around the fiber optic line.

20. The device of claim 13, wherein the two or more electromagnetic sensors are wrapped around a core that surrounds the fiber optic line.

21. The device of claim 20, wherein the core comprises at least one of a ferrite material, a mu-metal material, or a permalloy material.

22. The device of claim 13, wherein one of the two or more electromagnetic sensors is adhered to the fiber optic line by a ferrite epoxy.

23. The device of claim 13, wherein the structure comprises a catheter and/or guidewire.

24. The device of claim 13, wherein the first electromagnetic sensor is rotationally offset from the second electromagnetic sensor.

25. The device of claim 13, wherein the first electromagnetic sensor is rotationally offset from a longitudinal axis of the fiber optic line.

* * * * *